United States Patent [19]
Baber

[11] Patent Number: 5,152,769
[45] Date of Patent: Oct. 6, 1992

[54] APPARATUS FOR LAPAROSCOPIC SUTURING WITH IMPROVED SUTURE NEEDLE

[76] Inventor: Will Baber, 13 Elmwood Dr., Destrahan, La. 70047

[21] Appl. No.: 787,146

[22] Filed: Nov. 4, 1991

[51] Int. Cl.⁵ .............................................. A61B 17/04
[52] U.S. Cl. .................................... 606/145; 606/144; 606/139; 112/169
[58] Field of Search ............... 606/146, 147, 145, 144, 606/139, 148; 223/104; 112/169, 80.03, 185, 192, 194, 195, 227

[56] References Cited
U.S. PATENT DOCUMENTS

| | | | |
|---|---|---|---|
| 1,583,271 | 5/1926 | Biro | 606/144 |
| 4,440,171 | 4/1984 | Nomoto et al. | 606/145 |
| 4,462,395 | 7/1984 | Johnson | 606/100 |
| 4,596,249 | 6/1986 | Freda et al. | 606/145 |

Primary Examiner—Stephen C. Pellegrino
Assistant Examiner—Jeffrey A. Schmidt
Attorney, Agent, or Firm—Pravel, Gambrell, Hewitt, Kimball & Krieger

[57] ABSTRACT

A novel suturing assembly defined by a new and improved suturing needle, having a bore therethrough for forming an arc of thread to be grasped. The assembly would comprise a first and second barrel portion, the portions working to allow a rod member to secure the arc of thread formed, and hold it in place, while the needle forms a second suture, and secures the loop as part of the suture.

11 Claims, 8 Drawing Sheets

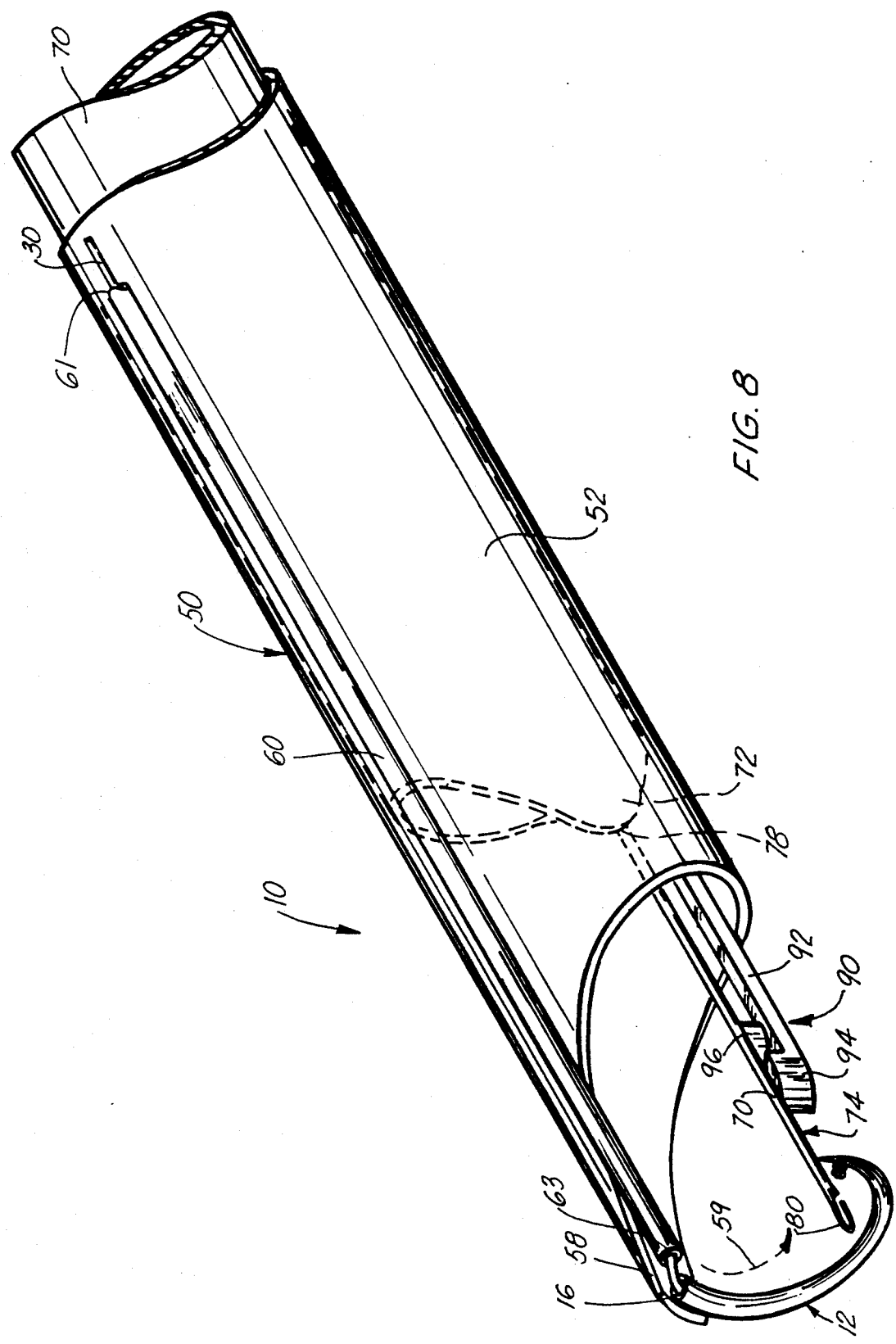

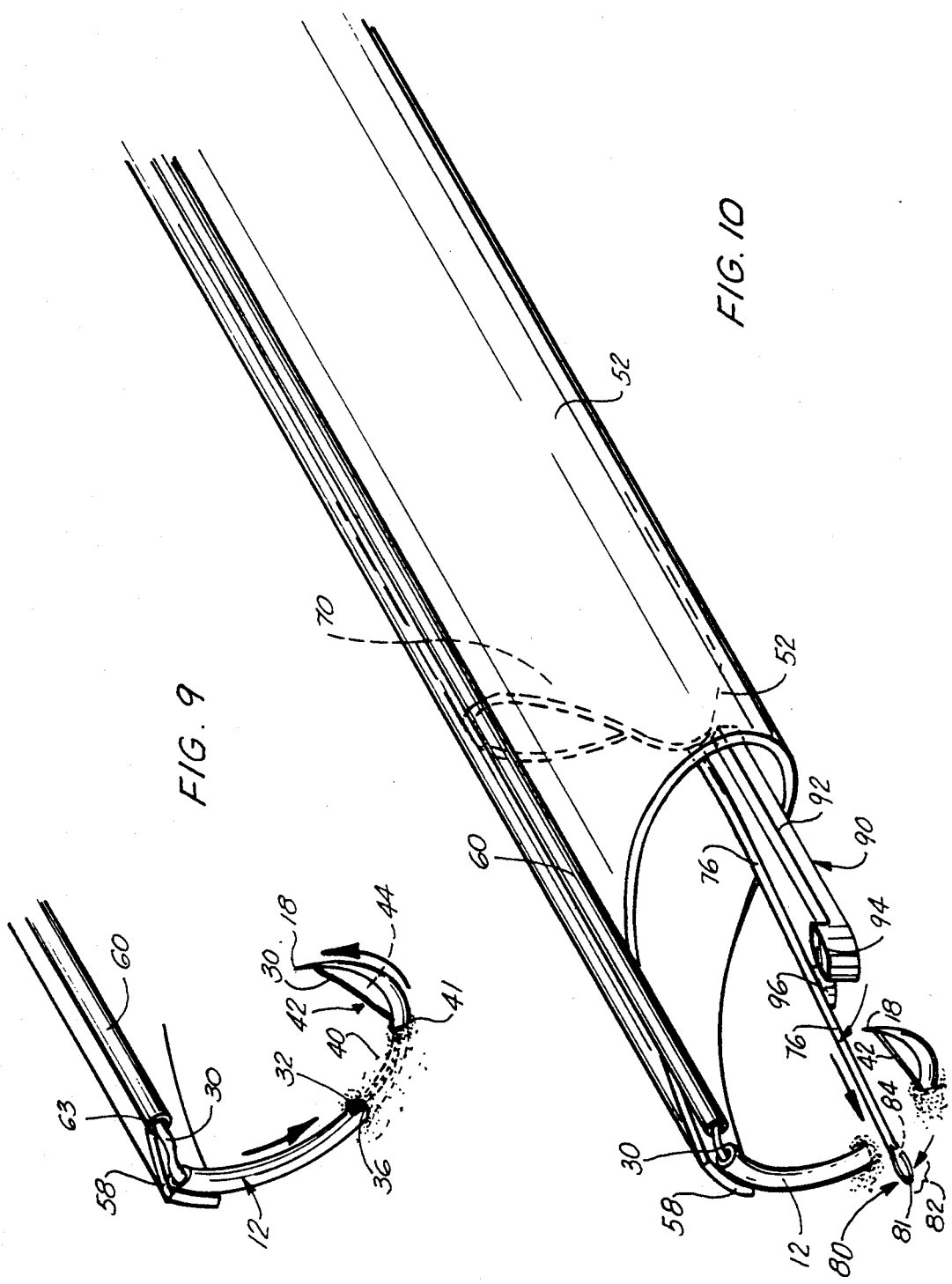

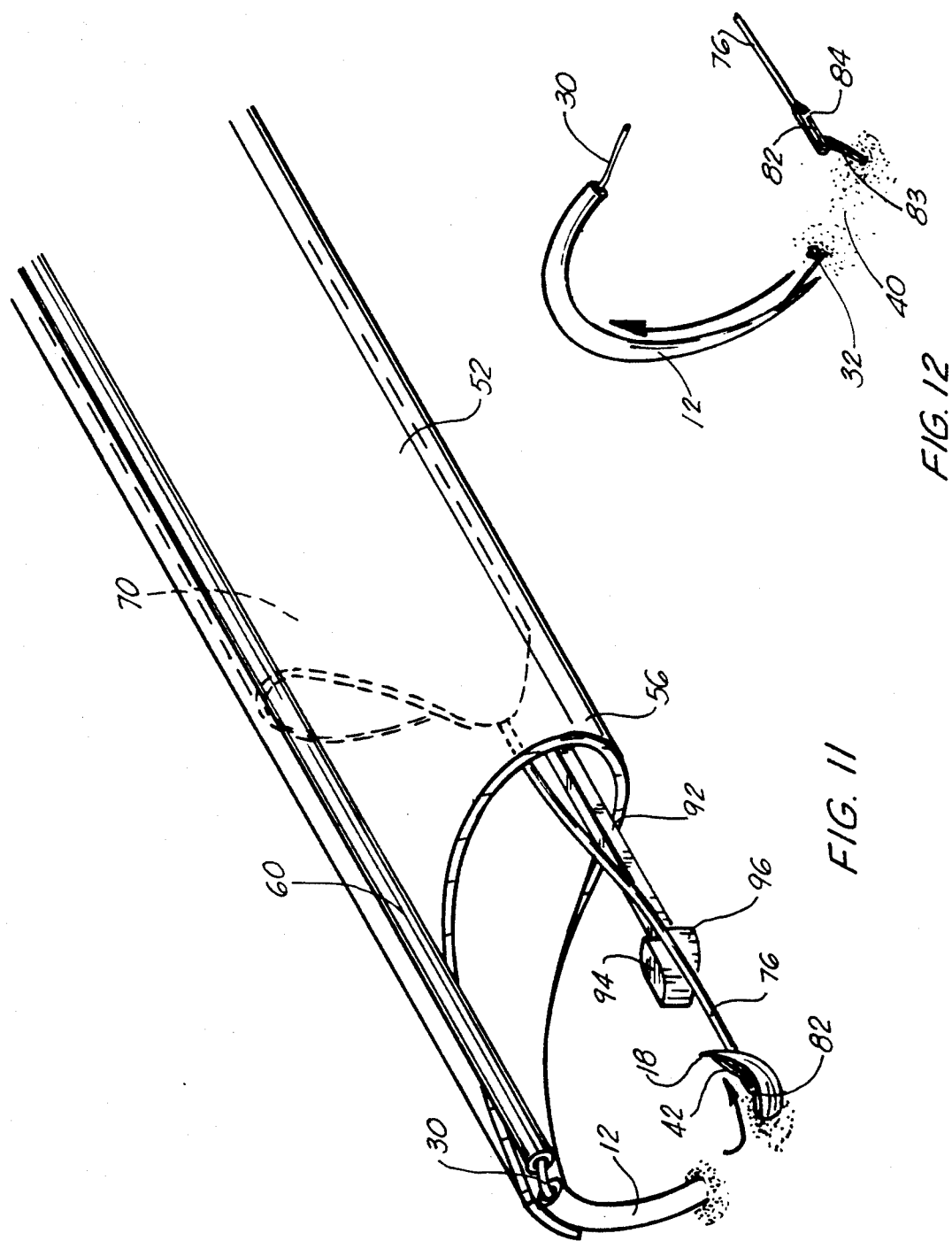

APPARATUS FOR LAPAROSCOPIC SUTURING WITH IMPROVED SUTURE NEEDLE

BACKGROUND OF THE INVENTION

1. Field of the Invention

The apparatus of the present invention relates to laparoscopic suturing, and to an improved needle used therefor. Moreover, the present invention relates to an apparatus which is utilized to suture incisions during laparoscopic surgery including a needle which provides a bore through its body to perform the suturing process.

2. General Background

In the general art of surgery of the type which uses a trocar, which is an instrument inserted, for example, into the abdominal wall wherein laparoscopic surgical instruments can be operated through the trocar, and the operation can be viewed by the surgeon through the use of fiber optics techniques during the surgery. Following the surgery through the use of a trocar, one must of course close any incisions which have been made within the abdominal cavity as a result of surgery. Therefore, there is a need for a type of suturing assembly which can be utilized through the trocar, so that the surgeon may insert it through the trocar tube and undertake the suturing of the incision without having to of course open the abdominal cavity.

Such a device would require a rather novel needle member, and the needle member would be used with an assembly that could be inserted through a port in the body wall, and the suturing could take place while viewed through a remote source, such as a viewing screen used with a fiber optic unit.

There have been a number of prior art patents issued on the general subject matter of suturing and the needles involved, the most common found in the art, being as follows:

| PATENT NO. | TITLE | ISSUE DATE |
| --- | --- | --- |
| 2,581,564 | Atraumatic Surgical Needle | Jan. 8, 1952 |
| 430,826 | Fish String Needle | Jun. 24, 1890 |
| 3,074,409 | Surgical Needle For Medical Purposes | Jan. 22, 1963 |
| 604,119 | Surgical Needle | May 17, 1898 |
| 1,757,129 | Atraumatic Rethreadable Surgical Needle | May 6, 1930 |
| 25 32 242 | Suturing Needle With Thread Feed And Release | Jul. 18, 1975 |
| 0,207,545 | Micro-Surgical Suture Needle | Jan. 1987 |
| 31 36 100 | Dutch Patent | Sep. 11, 1983 |

Other objects of the invention will be obvious to those skilled in the art from the following description of the invention.

SUMMARY OF THE PRESENT INVENTION

The apparatus of the present invention solves the shortcomings in the art in a simple and straightforward manner. What is provided is a novel suturing assembly which would be used in combination with a trocar for suturing incisions which have been made within, for example, the abdominal cavity of a patient, the assembly defined by a new and improved suturing needle, having a bore therethrough for forming an arc of thread to be grasped. The assembly would comprise a first and second barrel portion, the portions working to allow a rod member to secure the arc of thread formed, and hold it in place, while the needle forms a second suture, and secures the loop as part of the suture. There would be further provided means to align and guide the rod into position, within the body, and means to guide the thread along the assembly and through the bore in the needle wall.

Therefore, it is a principal object of the present invention to provide a novel suture assembly used in combination with a trocar, for suturing within the body cavity without having to make a large opening in the body to perform the suturing function;

It is a further object of the present invention to provide a suturing assembly having a novel suture needle for allowing the thread to be secured in such a manner to carry out the suturing function;

It is still a further object of the present invention to provide a suturing assembly which is safe and allows the suturing to be accomplished through guiding the assembly through the suturing process;

It is a further object of the present invention to provide a process of suturing a wound or incision within the body cavity utilizing an apparatus that can be manipulated from without the body during the suturing process; and It is a further object of the present invention to provide a novel suture needle for utilized in suturing within a body cavity through a trocar for housing the thread within a bore of the needle so that the thread is maintained relatively dry when it is pulled from the needle, and can be withdrawn for forming a loop to complete the suturing process.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 8 illustrates an overall perspective view of the suture assembly utilized in the present invention;

FIGS. 9 through 14 illustrate views of the suture assembly utilized in the present invention during the process of forming sutures with the present invention.

DETAILED DESCRIPTION OF THE PREFERRED EMBODIMENT

Figure 1:
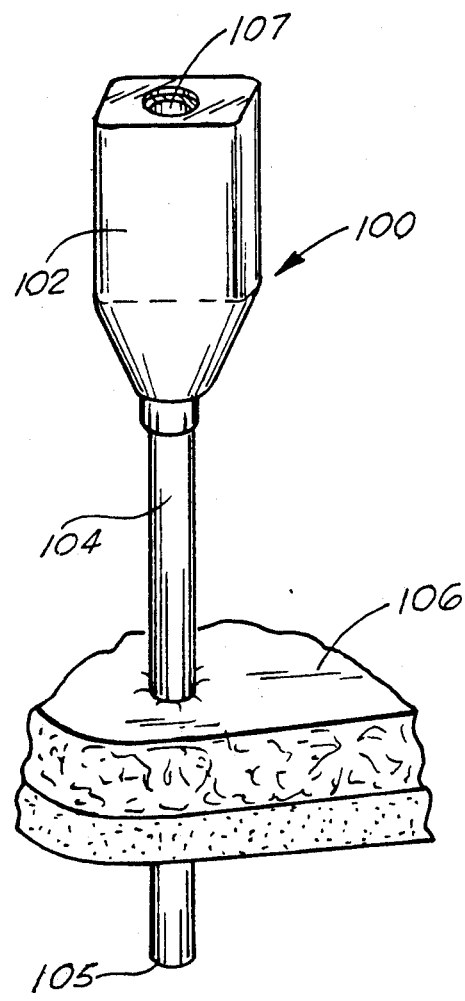
FIG. 1 illustrates a partial view of a laparoscopic trocar instrument inserted through the outer skin layer of a patent.
Figure 2:
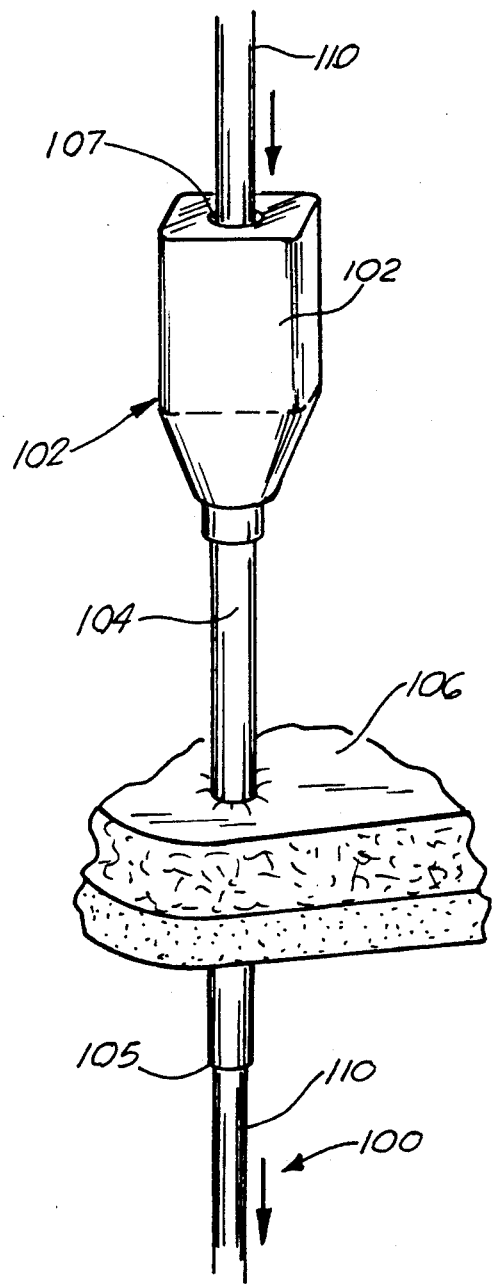
FIG. 2 illustrates an overall view of a laparoscopic trocar instrument accommodating the apparatus of the present invention.
Figure 3:
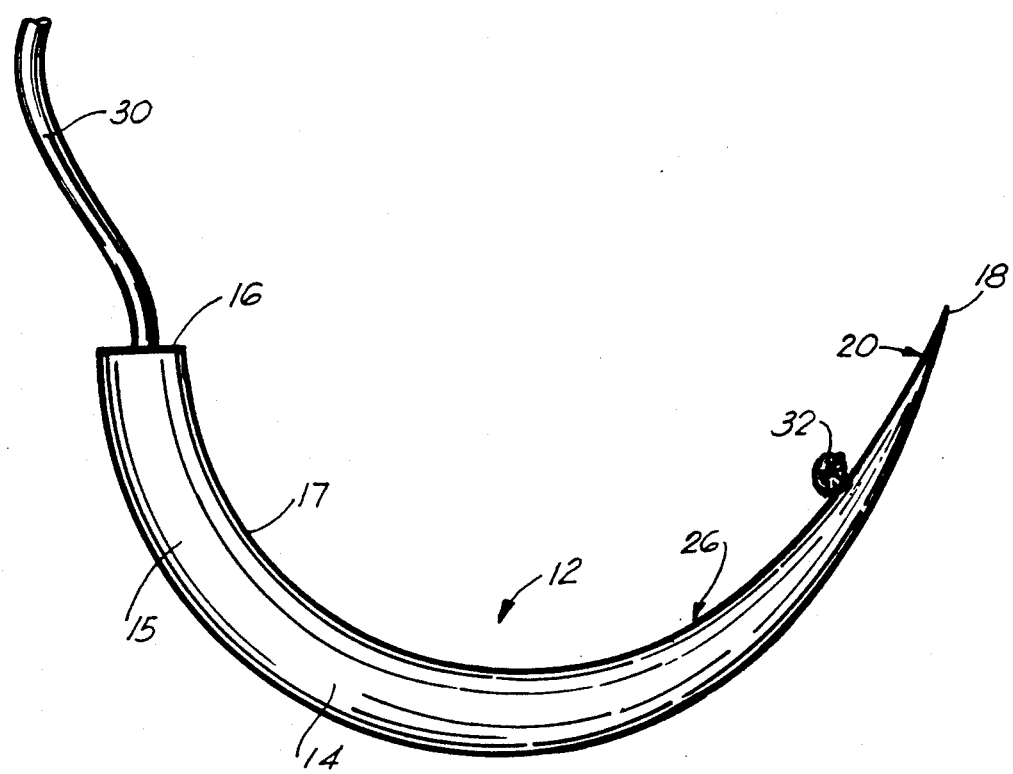
FIGS. 3 through 5 illustrate views of the preferred embodiment of the needle utilized in the present invention.
Figure 4:
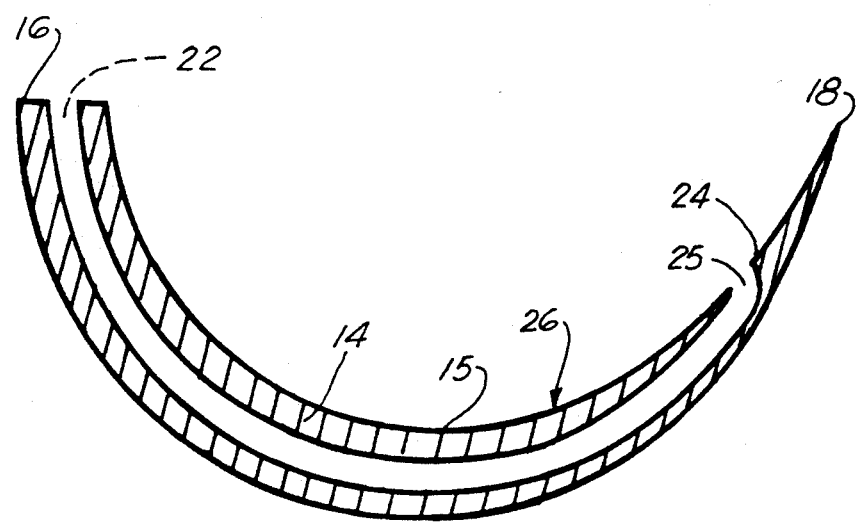
Figure 5:
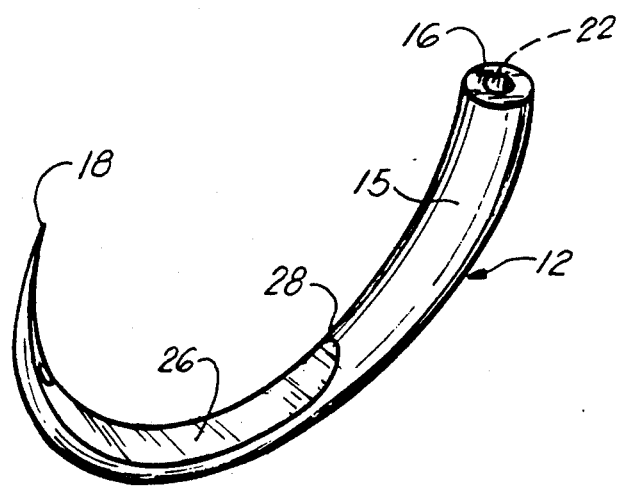
Figure 6:
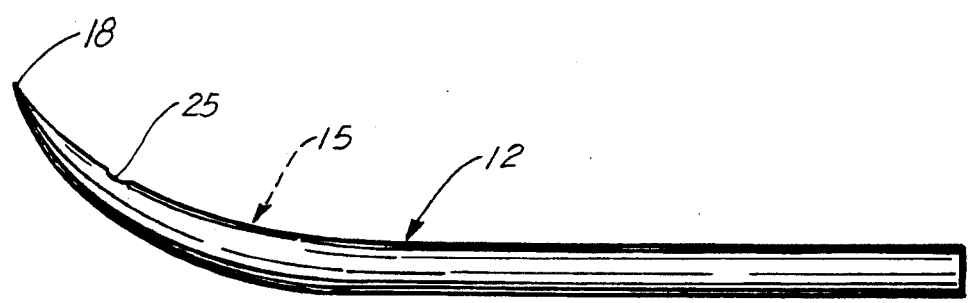
FIGS. 6 and 7 illustrate views of an alternate embodiment of the needle utilized in the present invention.
Figure 7:
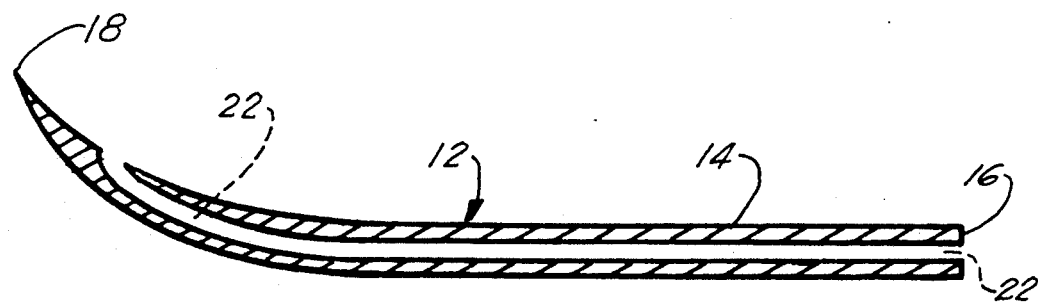
Figure 13:
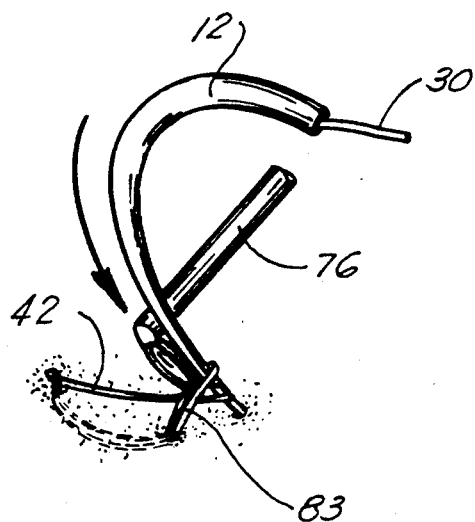

The preferred embodiment of the apparatus of the present invention is illustrated in the figures, with FIGS. 3 through 5 illustrating the preferred embodiment of the needle portion of the present invention, FIGS. 6 and 7 illustrating an alternate embodiment of the needle portion, and FIGS. 8 through 18 illustrating the preferred embodiment of the entire system of the present invention. Prior to a further discussion of the apparatus as illustrated in FIG. 3, reference is made to FIGS. 1 and 2 which illustrate a standard surgical instrument known as a trocar 100 which is common in the art of laparoscopic surgery and includes an upper body portion 102 and a lower housing portion 104, which in utilization the end 105 of housing 104 is inserted through a layer of skin 106 of a patient, so that surgical instruments 110, as seen in FIG. 2, may be utilized through the continuous bore 107 in instrument 100 and surgery can take place through the surgeon maneuvering the instruments outside of the patient while the surgical technique takes place through the trocar instrument 100. This is a common surgical technique and for purposes of this invention need not be explained further.

In general, what is provided in the present invention is a suture assembly 10 (see FIG. 8), which comprises a unique suturing needle 12, together with the remainder of the assembly 10 to be utilized within the needle 12. As discussed earlier, the assembly 10 would be utilized through the bore of a trocar 100, to suture openings or incisions made during surgery within the abdominal cavity of the body.

In the preferred embodiment, as illustrated in FIGS. 3 through 5, needle 12 would comprise an arcuate body portion 14, being larger and round on a first distal end 16, and taper to a point 18 on the forward end 20 of needle 12. Needle 12 would further comprise a bore 22 running through substantially the length of the needle body 14, commencing at the distal end 16 of the needle 12 to a point 24 along the needle body 14, adjacent the point 18 of the needle. The exterior wall 15 of the needle body 14, would further define a flat elongated section 26, extending substantially from the interior midpoint 28 of the needle body 14, along the interior curved wall 17 of the body to the point 18 of needle 12. The needle bore 22 would exit at a lower exit port 25 of the flat elongated section 26 as defined.

A length of thread 30 of the 12 needle would be threaded through the bore 22 at the distal end 16 of needle 12 and would be tied into knot 32 at the exit port 25 along the needle body 14. As seen in the drawings (See FIG. 9), when the needle point 18 is inserted into the layer of skin 40, the knot 32 formed at the lower exit port 25 of the flat section 26 of the needle 12 would be unable to slide through the bore 36 formed by the needle point 18 puncturing the skin, and would therefore remain on the outside of the skin as illustrated.

Upon the needle point 18 exiting the other side of the incision, the thread would be forced to form an arc 42, as illustrated, extending from the point 18 of needle 12, to the point of exit of the thread from the bore 41. The arc 42 formed by the thread would then define a grab space 44 in which the length of thread defining the line of the arc 42 could be grasped.

In its alternate embodiment, as illustrated in FIGS. 6 and 7, needle 12 would generally include a straight body portion 14, with the body portion 14 forming a curved portion 15 generally adjacent the point 18 of needle 12. There would also be formed, as with the principal embodiment, a bore 22, through the body of the needle 12, that would extend through the body 14, as previously described for FIGS. 3 through 5. In all other respects, however, as generally described in the preferred embodiment, the embodiment of needle 12 as illustrated in FIGS. 6 and 7 would function with the suturing assembly in the same manner as the preferred embodiment, as will be described further.

In either embodiments as illustrated, the bore within the needles 12 would enable the thread within the bore to be maintain relatively dry until such time as that length of thread is pulled in through the incision hole to be used in the suturing process.

At this point in the suturing process, apparatus 11 would further comprise a thread looping assembly means 50 would be utilized. As seen in FIGS. 8 through 14, assembly 50 would comprise an outer barrel portion 52, having an extended circular wall portion 54 and a forward end 56 forming an extended holding portion 58 secured to the large distal end 16 of the needle member 12. As illustrated, the needle 12 would be securely attached to the extended holding portion 58, with the curvature of the needle 12 being misaligned with the curvature, shown by arrow 59 of the wall 54 of the outer barrel portion 52 as illustrated, so that the needle 12 may be of longer length than the curvature of the barrel, and provide a greater ease for suturing as illustrated. This would provide that rotation of the barrel portion 52 would impart a rotation to needle 12 that is along a greater arc than the wall of outer barrel portion 52.

There would also be positioned on the outer wall 54 of the outer barrel portion 52 an extended thread housing 60 through which the thread 30 would be threaded, from its distal end 61 to its forward end 63, prior to the end of the thread being inserted into the needle 12 as illustrated. In this manner the thread could be guided through the thread housing 60 secured along the outer barrel 52, and be threaded directly into the needle bore 22 as the thread 30 exits the end 61 of the housing 60 as illustrated.

The extended outer barrel portion 52, with the thread housing secured along its wall, together with the curved needle 12 attached to the forward end of the barrel portion 52 would generally define one portion of the assembly. The barrel portion 52 of the present invention having needle 12 secured therethrough as illustrated in FIG. 12 can be utilized in and of itself as a stitching instrument. As illustrated, the needle having the thread threaded therethrough with a knot on the end portion would be pushed through the skin and the knot would be unable to pass through the incision hole. Upon forming a arc 42 as illustrated in FIG. 12, the needle could then be backed out from the hole with a loop 83 formed as illustrated. Then the needle would simply be rethreaded through the loop and in doing so, would form a chain stitch 30, as illustrated in FIG. 12. In this manner, the stitching would be accomplished without the use of the second portion of the instrument, but would be utilized simply with the barrel portion as seen in FIG. 12.

The second means of stitching would comprise the use of the barrel portion 52 in combination with the second portion of the apparatus. This second portion would comprise an additional means for securing and grasping the arc of thread formed by the needle as previously defined.

As illustrated, this second interior barrel portion 70, slidably engaged within the interior 53 of the outer barrel member 52 and moveable in relation thereto. As illustrated in the drawings, for the most part, since the interior barrel member 70 is encased within outer barrel 52, the barrel 70 is illustrated in phantom view.

As illustrated, interior barrel member 70 comprises a first end portion 72 have a thread grasping means 74 secured thereto. This means comprises a rod 76, attached at its first end 78 to the end 72 of the interior barrel member 70, and an open loop means 80 formed at its second end. The open loop means 80 is formed by a length of metal 81 curved into a loop 82, with a gap 84 formed therein, so that the length of thread 30 can be slid into the space 86 formed by the gap 84 and held in place when the rod 76 is pulled therefrom. In order to insure that the rod 76 with loop means 80 is in position to grasp the arc of thread 42, rod 76 includes a caming member 96 secured along its length to move forward as the interior tube 70 is pushed forward within outer tube 52. As illustrated in FIG. 8, there is provided a support arm 90 secured to the interior wall of outer tube 52, which likewise has a second caming means 94 on its end portion. As the rod 76 is pushed forward, caming means 96 makes contact with caming member 94 and the loop 80 is then pushed to the side, which enables it to be misaligned with arc 42 so that it can get pass the arc after caming means 96 moves passed means 94. Rod 76 is then moved back into alignment and the loop is directly aligned with the arc of thread 42. In that manner, when the rod 76 is retrieved rearwardly, arc of thread 42 will be caught within loop 80 and the loop will be securely in place, without the fear of the loop being pulled back in through the incision.

Figure 14:
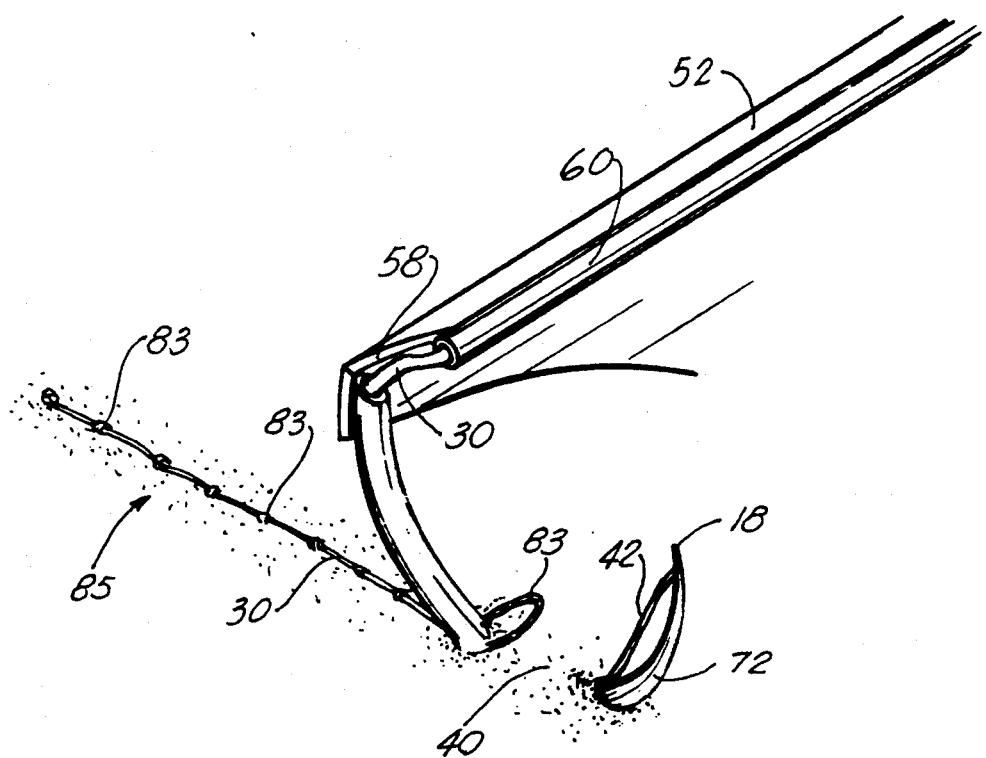
Figure 15:
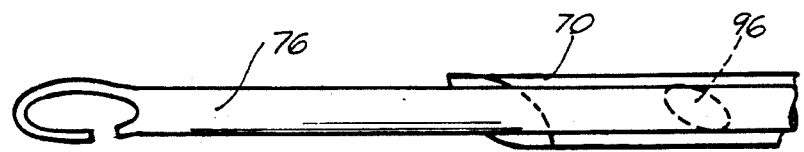
FIGS. 15 through 18 illustrate representational views of the thread grasping portion of the assembly of the present invention.

Following that step, the point of the needle 12, would then be moved through the loop of thread (See FIG. 13), and would be threaded through the skin to form another suture (See FIG. 14). When the needle 12 is maneuvered in such a manner, then the length of thread 30 would be held in place to close and form a continuing suture 85 as the loop 83 would tighten around the thread 30 as illustrated in FIG. 14.

Figure 16:
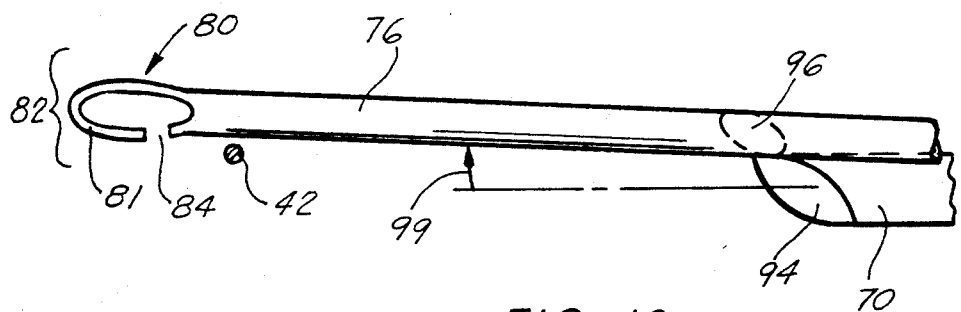
Figure 17:
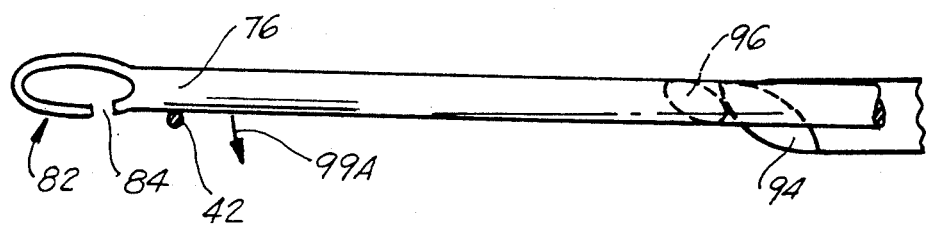
Figure 18:
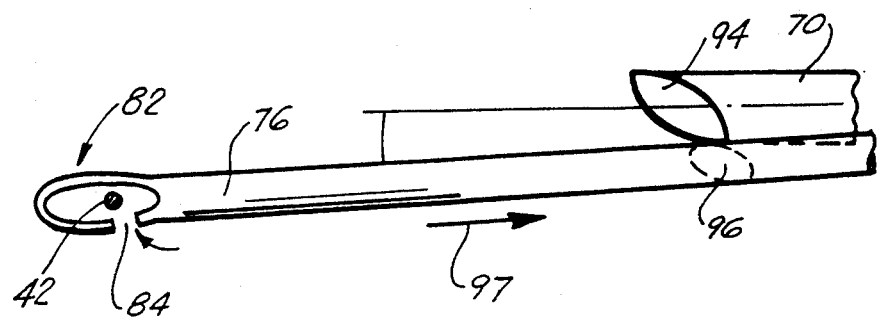

FIGS. 15 through 18 illustrate a representational view of the rod member 76 as it is maneuvering from within the outer barrel member 52, during the suturing process. It is clear that the rod member 76 must maneuver itself to several positions as illustrated in order to carry out the suturing function as seen in these Figures. For example, rod member 76 in FIG. 15 which illustrates loop 80, and the caming means 96 as the rod member is moving through the outer tube. FIG. 16 illustrate caming member 96 making contact with caming member 94 of rod 92, and therefore the rod 76 is misaligned a degree indicated by arrow 99 in FIG. 16. This misalignment as stated earlier, would therefore allow the loop 80 to move pass the arc of thread as illustrated in cross section in FIG. 16. Once the caming member 96 has moved pass the caming member 94, the rod 76 is moved back into the aligned position of FIG. 15, in the direction of arrow 99A. It therefore has moved pass the arc of thread. As seen in FIG. 18, upon being returned back in the direction of arrow 97 into the outer barrel, the caming member 96 would then move pass the second side of caming member 94 which would move the loop into a position so that as it passed thread 42, the thread 42 would naturally slide into opening 84 into the loop 80 as illustrated in FIG. 18. Therefore, this caming action between the inner tube and the outer tube would guarantee that the thread is caught within the end of the tube 76 and therefore the suturing process can take place.

Once caming means 96 has moved pass caming means 94, rod 76 is in place, the interior tube 70 would then be withdrawn from the outer tube slowly. At this point the caming means 96 would move pass the second side of caming means 94 and would be misaligned in the direction of thread 42. In doing so, as the rod is pulled back, the thread 42 would be in contact with the surface of rod 76 and when it came into contact with opening 84, it would slip into the opening and be caught within the loop at the end of rod 96.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A suturing assembly, comprising:
   a) a first outer barrel having a first end portion, and a second end portion, and an interior bore therethrough, said barrel portion further including a first caming means has been;
   b) a suture needle secured to the second of the barrel portion, the suture needle including a bore through the needle body portion and a thread therethrough;
   c) a second barrel portion, slidably moveable within the bore of the outer barrel, likewise having a first and second end portions, and a bore therethrough;
   d) rod means on the second end of the second barrel portion, said rod means further comprising a loop member for engaging a length of thread;
   e) second caming means on the rod means for engaging the first camming means on the first outer barrel, for misaligning the end of the rod means as the rod means moves to a position past the length of the thread and
   f) a trocar for positioning the suturing apparatus from a position outside to inside of the body cavity.

2. The assembly in claim 1, further comprising a housing means secured along the length of the outer barrel through which the thread is threaded before the thread is threaded through the needle member.

3. The suturing assembly in claim 1, wherein the loop member secures an arc of thread, to allow the repetition of the needle to suture therethrough.

4. A process for forming sutures within the confines of the body without forming a direct incision in the skin, comprising the following steps:
   a) providing a suture assembly, formed by a pair of slidingly engagable barrel members, a first end of which are insertable into a trocar member extending into the body cavity of the patient;
   b) providing a suture needle on the first end of the outer barrel member, the needle having a length of thread therethrough;
   c) rotating the barrel so that the suture needle punctures the tissue to be sutured, forming an arc of thread through the puncture;
   d) grasping and securing the arc to form a loop of thread;
   e) withdrawing the needle from the tissue by rotating the needle back through the puncture;
   f) rotating the needle through the loop of thread to complete the suture;
   g) repeating steps c through e until the tissue is completely sutured.

5. The process in claim 4, wherein the arc of thread grasped is secured by a loop means secured to a rod member extending from the barrel.

6. The process in claim 4, further comprising the step of camming the loop means for engaging the thread to be formed into a suture.

7. A suturing assembly, comprising:

a) a first outer barrel having a first end portion, and a second end portion, and an interior bore therethrough, said barrel portion further including a first caming means;
b) a suture needle secured to the second end of the barrel portion, the suture needle including a bore through the needle body portion for threading thread therethrough;
c) a second barrel portion, slidably moveable within the bore of the outer barrel, likewise having a first and second end portions, and a bore therethrough;
d) means on the second end of the second barrel portion, said means further comprising a loop member for engaging the of thread;
e) second caming means on the rod means for engaging the first camming means on the first outer barrel, to misalign the loop means as the loop means moves to a position past the length of the thread, and
f) a trocar member insertable into the cavity of the patient for positioning the suturing apparatus from a position outside to inside of the body cavity.

8. The assembly in claim 7, further comprising a housing means secured along the length of the exterior barrel through which the thread is threaded before the thread is threaded through the needle member.

9. The suturing assembly in claim 7, wherein the loop means secures the arc of thread, to allow the continuing suturing of the needle therethrough.

10. The suturing assembly in claim 7, wherein the first and second camming means provide a means to allow the loop means to secure the arc of thread, and to return the secured thread into a loop for suturing.

11. The suturing assembly in claim 7, wherein the needle member is circumferentially misaligned in relation to the curvature of the barrel member, so as to provide a longer needle length for suturing.

* * * * *